(12) United States Patent
Gordon et al.

(10) Patent No.: US 10,788,829 B2
(45) Date of Patent: Sep. 29, 2020

(54) SELF-DRIVING VEHICLE PASSENGER MANAGEMENT

(71) Applicant: International Business Machines Corporation, Armonk, NY (US)

(72) Inventors: Michael S. Gordon, Yorktown Heights, NY (US); Jinho Hwang, Ossining, NY (US); Roxana Monge Nunez, San Jose (CR); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 208 days.

(21) Appl. No.: 15/848,187

(22) Filed: Dec. 20, 2017

(65) Prior Publication Data
US 2019/0187704 A1 Jun. 20, 2019

(51) Int. Cl.
G05D 1/00 (2006.01)
G05D 1/02 (2020.01)
(Continued)

(52) U.S. Cl.
CPC .......... *G05D 1/0088* (2013.01); *B60W 40/08* (2013.01); *G01C 21/3484* (2013.01);
(Continued)

(58) Field of Classification Search
CPC .... B60W 30/025; B60W 50/14; B60W 10/30; B60W 10/20; B60W 50/0098; B60W 40/08; B60W 60/00; G06F 3/013; G06F 3/015; G06F 3/017; G06F 21/32; B60N 2/002; B60N 2/0244; B60N 2/0276; B60N 2/02; B60N 2/0224; A61B 5/18; A61B 5/0205; A61B 5/6893; A61B 5/024; A61B 5/00; G06K 9/00838; G06K 9/00845; G06K 9/00348; G06K 9/00261; G06K 9/00382; G06K 9/00805; G06K 9/00255; G06K 9/00288; G06K 9/00355; B60K 28/00;
(Continued)

(56) References Cited

U.S. PATENT DOCUMENTS 6,104,293 A 8/2000 Rossi
6,922,147 B1 7/2005 Viksnins et al.
(Continued)

OTHER PUBLICATIONS

P. Mell et al., "The NIST Definition of Cloud Computing", National Institute of Standards and Technology, Information Technology Laboratory, Sep. 2011, pp. 1-7.
(Continued)

*Primary Examiner* — Behrang Badii
(74) *Attorney, Agent, or Firm* — Law Office of Jim Boice

(57) ABSTRACT

A computer-implemented method controls a self-driving vehicle. One or more processors, based on a set of sensor readings from one or more passenger sensors within a self-driving vehicle (SDV), determine an identity of a current passenger in the SDV. The processor(s) establish a destination for the current passenger in the SDV based on the identity of the current passenger in the SDV, and receive computer executable instructions directing the SDV to travel to the destination for the current passenger in the SDV. The processor(s) then execute the computer executable instructions to cause the SDV to travel to the destination.

18 Claims, 6 Drawing Sheets

(51) Int. Cl.
G01C 21/34 (2006.01)
B60W 40/08 (2012.01)
G01C 21/36 (2006.01)
A61B 5/18 (2006.01)
A61B 5/0205 (2006.01)
A61B 5/00 (2006.01)
B60W 50/00 (2006.01)
G06F 3/01 (2006.01)

(52) U.S. Cl.
CPC ....... *G01C 21/3617* (2013.01); *G05D 1/0246* (2013.01); *A61B 5/00* (2013.01); *A61B 5/0205* (2013.01); *A61B 5/18* (2013.01); *B60W 50/00* (2013.01); *G06F 3/01* (2013.01)

(58) Field of Classification Search
CPC .. G05D 1/0055; G05D 1/0088; G05D 1/0246; G06N 3/006; G06N 5/046; G06N 20/00; B62D 1/181; G01C 21/3617; G01C 21/3484; B60G 17/0195; G07C 9/00571; G07C 9/37; B60R 25/25; G07B 15/00; G10L 17/22; G06Q 30/0645
See application file for complete search history.

(56) References Cited

U.S. PATENT DOCUMENTS

| | | |
|---|---|---|
| 7,319,382 B1 | 1/2008 | Vu |
| 7,714,737 B1 | 5/2010 | Morningstar |
| 9,266,535 B2 | 2/2016 | Schoenberg |
| 9,457,689 B2 | 10/2016 | Stefan et al. |
| 2003/0122662 A1 | 7/2003 | Quinonez |
| 2009/0079557 A1 | 3/2009 | Miner |
| 2009/0146813 A1 | 6/2009 | Nuno |
| 2014/0184404 A1 | 7/2014 | Schoenberg et al. |
| 2014/0306838 A1 | 10/2014 | Beumler |
| 2018/0319407 A1* | 11/2018 | Lisseman ........... G06K 9/00838 |
| 2018/0333093 A1* | 11/2018 | Gallagher ............ A61B 5/0205 |
| 2019/0051069 A1* | 2/2019 | Cooley .............. G06K 9/00348 |
| 2019/0101985 A1* | 4/2019 | Sajda ..................... G06F 3/017 |
| 2019/0126914 A1* | 5/2019 | Nojoumian .......... G05D 1/0088 |
| 2019/0187704 A1* | 6/2019 | Gordon .............. G01C 21/3617 |

OTHER PUBLICATIONS

Lisetti et al., "Using Noninvasive Wearable Computers to Recognize Human Emotions from Physiological Signals". Hindawi Publishing Corporation, Eurasip Journal on Applied Signal Processing 2004: 11, pp. 1672-1687.

Olga Khazan, "This App Reads Your Emotions on Your Face". The Atlantic Monthly Group, The Atlantic, Jan. 15, 2014. Web Nov. 22, 2016. <http://www.theatlantic.com/technology/archive/2014/01/this-app-reads-your-emotions-on-your-face/282993/>.

Anonymous, "Dog Monitor". Tappytaps, 2015. Web Nov. 22, 2016. <http://www.dogmonitorapp.com/>.

Mendl et al., "An integrative and functional framework for the study of animal emotion and mood". Proceedings of the Royal Society B, Biological Sciences, Aug. 4, 2010. Web Nov. 22, 2016. <http://rspb.royalsocietypublishing.org/CONTENT/277/1696/2895#page>.

* cited by examiner

SELF-DRIVING VEHICLE PASSENGER MANAGEMENT

TECHNICAL FIELD

The present invention relates to the field of vehicles, and specifically to the field of self-driving vehicles. Still more specifically, the present invention relates to the field of controlling self-driving vehicles based on the passengers of the self-driving vehicles.

SUMMARY

In one or more embodiments of the present invention, a computer-implemented method controls a self-driving vehicle. One or more processors, based on a first set of sensor readings from one or more passenger sensors within a self-driving vehicle (SDV), determine an identity of a current passenger in the SDV. The processor(s) determine, based on a second set of sensor readings from the one or more passenger sensors within the self-driving vehicle SDV, a current emotional state and a current physiological state of the current passenger in the SDV. The processor(s) establish a destination for the current passenger in the SDV based on the identity, current emotional state, and current physiological state of the current passenger in the SDV, and receive computer executable instructions directing the SDV to travel to the destination for the current passenger in the SDV. The processor(s) then execute the computer executable instructions to cause the SDV to travel to the destination for the current passenger in the SDV.

In one or more embodiments of the present invention, the method is implemented as a computer program product and/or in a system.

DETAILED DESCRIPTION

Figure 1:
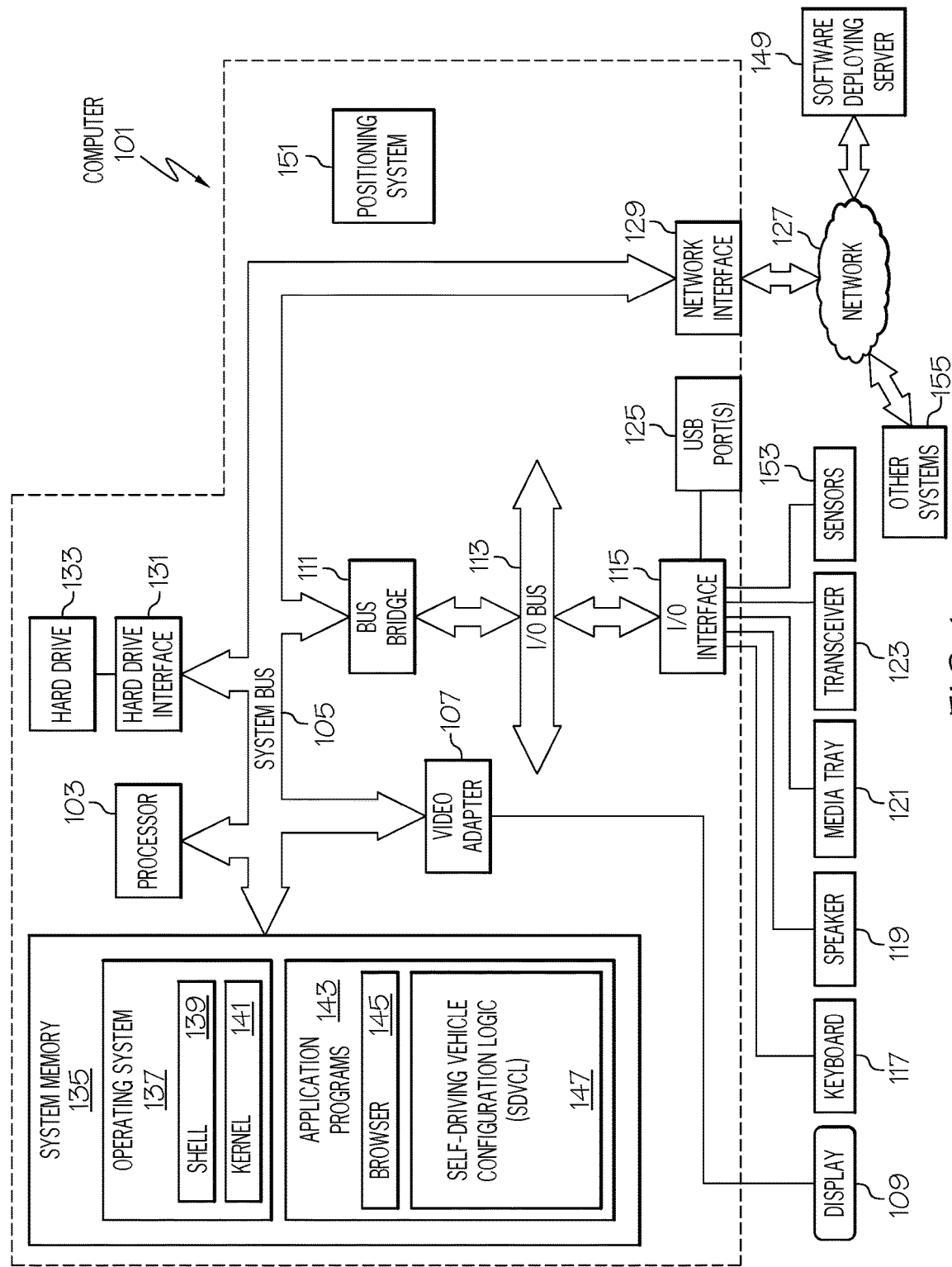
FIG. 1 depicts an exemplary system and network in which the present invention may be implemented.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be implemented within software deploying server 149 and/or other systems 155 shown in FIG. 1, and/or supervisory computer 201 and/or adjusted passenger monitoring system 214 shown in FIG. 2, and/or a self-driving vehicle (SDV) on-board computer 301 shown in FIG. 3.

Exemplary computer 101 includes a processor 103 that is coupled to a system bus 105. Processor 103 may utilize one or more processors, each of which has one or more processor cores. A video adapter 107, which drives/supports a display 109 (which may be a touch screen capable of receiving touch inputs), is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a camera 117 (capable of taking digital photographs and/or videos), a speaker 119, a media tray 121 (which may include storage devices such as CD-ROM drives, multi-media interfaces, etc.), a transceiver 123 (capable of transmitting and/or receiving electronic communication signals), and external USB port(s) 125. While the format of the ports connected to I/O interface 115 may be any known to those skilled in the art of computer architecture, in one embodiment some or all of these ports are universal serial bus (USB) ports.

Figure 2:
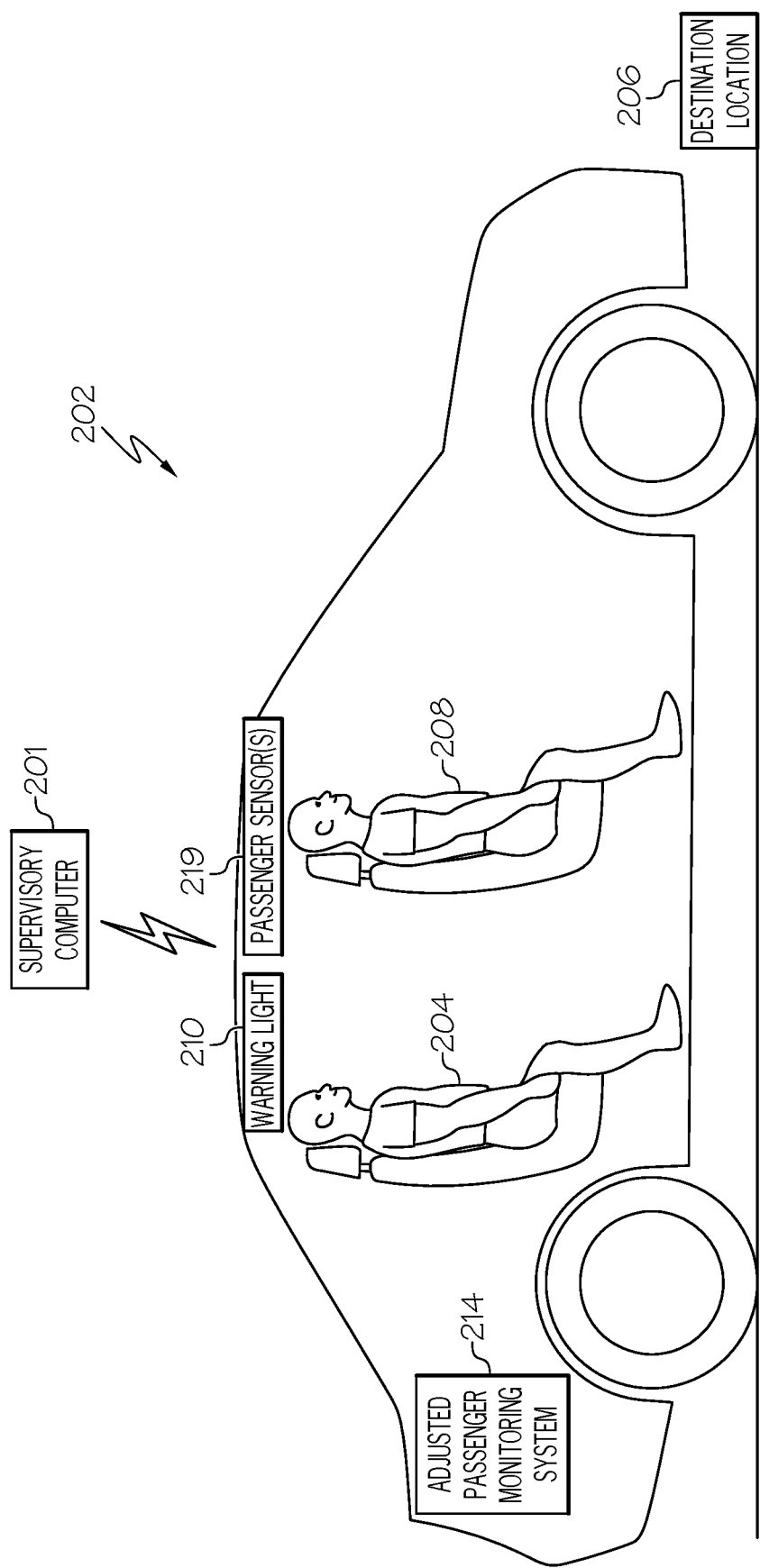
FIG. 2 illustrates an exemplary self-driving vehicle (SDV) delivering a passenger to a destination location in accordance with one or more embodiments of the present invention.

As depicted, computer 101 is able to communicate with a software deploying server 149 and/or other systems 155 (e.g., establishing communication between one of the other systems 155 such as supervisory computer 201 and SDV 202 shown in FIG. 2) using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include Self-Driving Vehicle Configuration Logic (SDVCL) 147. SDVCL 147 includes code for implementing the processes described below, including those described in FIGS. 2-4. In one embodiment, computer 101 is able to download SDVCL 147 from software deploying server 149, including in an on-demand basis, wherein the code in SDVCL 147 is not downloaded until needed for execution. In one embodiment of the present invention, software deploying server 149 performs all of the functions associated with the present invention (including execution of SDVCL 147), thus freeing computer 101 from having to use its own internal computing resources to execute SDVCL 147.

Also within computer 101 is a positioning system 151, which determines a real-time current location of computer 101 (particularly when part of a self-driving vehicle as described herein). Positioning system 151 may be a combination of accelerometers, speedometers, etc., or it may be a global positioning system (GPS) that utilizes space-based satellites to provide triangulated signals used to determine two-dimensional or three-dimensional locations.

Also associated with computer 101 are sensors 153, which detect an environment of the computer 101 and/or the state of occupants and/or occupants' possessions in a self-driving vehicle (SDV). More specifically, when detecting the environment of the SDV, sensors 153 are able to detect vehicles, road obstructions, pavement, etc. For example, if computer 101 is on board a self-driving vehicle (SDV), then sensors 153 may be cameras, radar transceivers, etc. that allow the SDV to detect the environment (e.g., other vehicles, road obstructions, pavement, etc.) of that SDV, thus enabling it to be autonomously self-driven. Similarly, sensors 153 may be cameras, thermometers, microphones (e.g., microphone 331 shown in FIG. 3), light sensors such as light sensor 329 shown in FIG. 3 for detecting how dark a roadway is, chemical sensors for detecting chemical spills on a roadway, moisture detectors, etc. that detect ambient weather conditions, traffic conditions (as detected by the cameras, microphones, etc.), and other environmental conditions of a roadway upon which the SDV is traveling. Furthermore, sensors 153 may be cameras, microphones, weight scales, etc. that detect the presence and/or state of passengers in the SDV.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

Self-driving vehicles (SDVs) are vehicles that are able to autonomously drive themselves through private and/or public spaces. Using a system of sensors that detect the location and/or surroundings of the SDV, logic within or associated with the SDV controls the speed, propulsion, braking, and steering of the SDV based on the sensor-detected location and surroundings of the SDV.

With reference now to FIG. 2, an exemplary self-driving vehicle (SDV) 202 is depicted in accordance with one or more embodiments of the present invention. Assume that SDV 202 has picked up a passenger 204, and will deliver the passenger 204 to a destination location 206, per the instructions of an on-board computer (e.g., SDV on-board computer 301 shown in FIG. 1).

Figure 3:
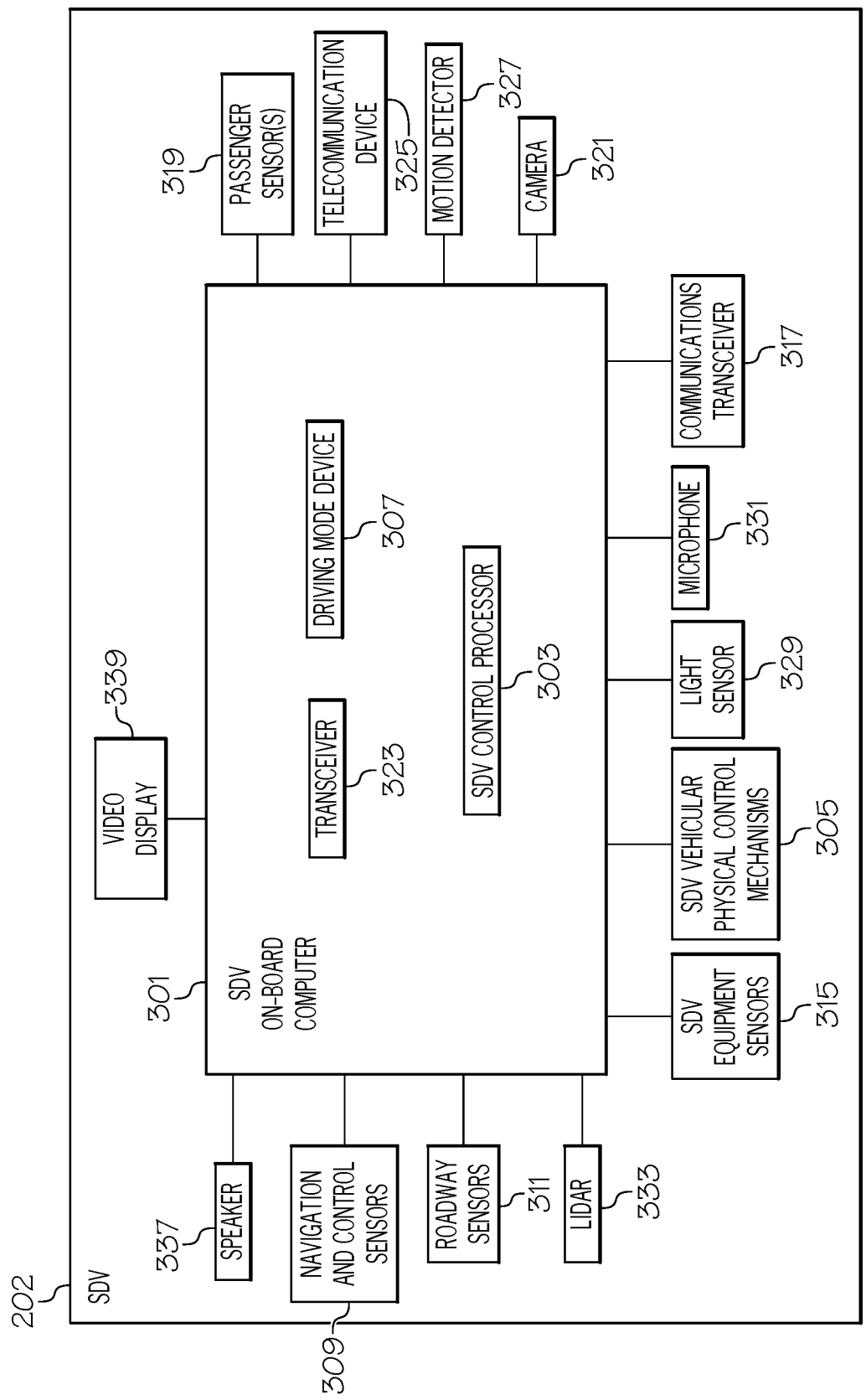
FIG. 3 depicts additional exemplary detail within an SDV in accordance with one or more embodiments of the present invention.

SDV 202 may be programmed to travel to destination location 206 (e.g., by entering an address for the destination location in a display such as video display 339 shown in FIG. 3). However, this destination may be wrong. For example, assume that a primary passenger 208 (e.g., who is sitting up front in what would be the driver's seat in a traditional vehicle or in an SDV whose operations are capable of being taken over by a human) has programmed the SDV 202 to drive to his/her office, while forgetting or not knowing that passenger 204 is also in the SDV 202. That is, assume that passenger 204 is a child of the primary passenger 208 who needs to be dropped off at daycare, rather than accompanying his/her parent to work. The present invention will detect and identify passenger 204, and will override the input of primary passenger 208, in order to drop off passenger 204 at his/her daycare first before continuing on to the workplace of primary passenger 208.

In an embodiment of the present invention, when the system (e.g., supervisory computer 201 shown in FIG. 2 and/or SDV on-board computer 301 shown in FIG. 3) determines that there is a passenger (e.g., passenger 204) in SDV 202 and re-routes the SDV 202 to travel to the destination of the passenger 204 (e.g., daycare), the primary passenger 208 is given a warning, in order to avoid any consternation that may result from the SDV 202 not going directly to the original destination location 206. For example, an alert on a smart phone carried by the primary passenger 208, or on a dashboard display inside SDV 202, will let the primary passenger 208 know what is happening.

In an embodiment of the present invention, the destination location 206 is entered into an app on a smart phone. This app then directs a supervisory computer (e.g., supervisory computer 201 shown in FIG. 2) to direct SDV 202 to travel to the destination location 206.

The detection of passenger 204, which is detected by passenger sensor(s) 219, which are analogous to passenger sensor(s) 319 shown in FIG. 3, may be according to a modifiable vigilance level V (discussed below), thereby creating an adjusted passenger monitoring system 214.

The adjusted passenger monitoring system 214 includes a processing system (e.g., processor 103 shown in FIG. 1), sensors (e.g., sensors 153 shown in FIG. 1), etc. that 1) determine the presence of passenger 204, 2) determine an identity of passenger 204, 3) determine where passenger 204 is supposed to be going, and 4) control operations of the SDV 202 (e.g., by sending signals to the SDV on-board computer 301 shown in FIG. 3) based on the identity and/or state of passenger 204.

With reference now to FIG. 3, additional details of one or more embodiments of the SDV 202 shown in FIG. 2 are presented.

As shown in FIG. 3, SDV 202 has an SDV on-board computer 301 that controls operations of the SDV 202. According to directives from a driving mode device 307, the SDV 202 can be selectively operated in manual mode ("human driven") or autonomous ("fully computer controlled") mode. In some embodiments, driving mode device 307 is a dedicated hardware device that selectively directs the SDV on-board computer 301 to operate the SDV 202 in one of the autonomous modes or in the manual mode.

While in autonomous mode, SDV 202 operates without the input of a human driver, such that the engine, steering mechanism, braking system, horn, signals, etc. are controlled by the SDV control processor 303, which is now under the control of the SDV on-board computer 301. That is, by the SDV on-board computer 301 processing inputs taken from navigation and control sensors 309 and the driving mode device 307 (indicating that the SDV 202 is to be controlled autonomously), then driver inputs to the SDV control processor 303 and/or SDV vehicular physical control mechanisms 305 are no longer needed.

As just mentioned, the SDV on-board computer 301 uses outputs from navigation and control sensors 309 to control the SDV 202. Navigation and control sensors 309 include hardware sensors that 1) determine the location of the SDV 202; 2) sense other cars and/or obstacles and/or physical structures around SDV 202; 3) measure the speed and direction of the SDV 202; and 4) provide any other inputs needed to safely control the movement of the SDV 202.

With respect to the feature of 1) determining the location of the SDV 202, this can be achieved through the use of a positioning system such as positioning system 151 shown in FIG. 1. Positioning system 151 may use a global positioning system (GPS), which uses space-based satellites that provide positioning signals that are triangulated by a GPS receiver to determine a 3-D geophysical position of the SDV 202. Positioning system 151 may also use, either alone or in conjunction with a GPS system, physical movement sensors such as accelerometers (which measure acceleration of a vehicle in any direction), speedometers (which measure the instantaneous speed of a vehicle), airflow meters (which measure the flow of air around a vehicle), etc. Such physical movement sensors may incorporate the use of semiconductor strain gauges, electromechanical gauges that take readings from drivetrain rotations, barometric sensors, etc.

With respect to the feature of 2) sensing other cars and/or obstacles and/or physical structures around SDV 202, the positioning system 151 may use radar or other electromagnetic energy that is emitted from an electromagnetic radiation transmitter (e.g., transceiver 323 shown in FIG. 3), bounced off a physical structure (e.g., another car), and then received by an electromagnetic radiation receiver (e.g., transceiver 323). An exemplary positioning system within SDV 202 is a Light Detection and Ranging (LIDAR) (e.g., LIDAR 333 shown in FIG. 3) or Laser Detection and Ranging (LADAR) system that measures the time it takes to receive back the emitted electromagnetic radiation (e.g., light), and/or evaluates a Doppler shift (i.e., a change in frequency to the electromagnetic radiation that is caused by the relative movement of the SDV 202 to objects being interrogated by the electromagnetic radiation) in the received electromagnetic radiation from when it was transmitted, the presence and location of other physical objects can be ascertained by the SDV on-board computer 301. In one or more embodiments, different SDVs are able to directly communicate with one another in order to let one another know their relative positions. That is, a first SDV may transmit its GPS coordinates to a second SDV (and vice versa), thus allowing the first SDV and the second SDV to know the current real-time GPS-coordinate location of the other SDV.

With respect to the feature of 3) measuring the speed and direction of the SDV 202, this can be accomplished by taking readings from an on-board speedometer (not depicted) on the SDV 202, by successive locations as measured by an on-board GPS system, and/or detecting movements to the steering mechanism (also not depicted) on the SDV 202 and/or the positioning system 151 discussed above.

With respect to the feature of 4) providing any other inputs needed to safely control the movement of the SDV 202, such inputs include, but are not limited to, control signals to activate a horn, turning indicators, flashing emergency lights, etc. on the SDV 202.

In one or more embodiments of the present invention, SDV 202 includes roadway sensors 311 that are coupled to the SDV 202. Roadway sensors 311 may include sensors that are able to detect the amount of water, snow, ice, etc. on the roadway 203 (e.g., using cameras, heat sensors, moisture sensors, thermometers, etc.). Roadway sensors 311 also include sensors that are able to detect "rough" roadways (e.g., roadways having potholes, poorly maintained pavement, no paving, etc.) using cameras, vibration sensors, etc. Roadway sensors 311 may also include sensors that are also able to detect how dark the roadway 203 is using light sensors.

In one or more embodiments of the present invention, a camera 321 can be movably trained on roadway 203, in order to provide photographic images of conditions on the roadway 203 upon which the SDV 202 is traveling. In one or more embodiments of the present invention, the camera 321 will compare real-time images of roadway 203 with past images of roadway 203, in order to determine any changes to the condition of the roadway 203.

In one or more embodiments of the present invention, camera 321 can also be trained on passengers (e.g., passenger 204 and/or primary passenger 208 shown in FIG. 2). That is, camera 321 can take a still photo or a video of passengers while they are inside of SDV 202. In a preferred embodiment, there are actually two cameras (depicted as camera 321). A first camera is aimed as the interior cabin of the SDV 202, while the second camera is aimed at the exterior of SDV 202 (e.g., the roadway and external components of SDV 202, such as its tires).

In one or more embodiments of the present invention, also within the SDV 202 are SDV equipment sensors 315. SDV equipment sensors 315 may include cameras aimed at tires on the SDV 202 to detect how much tread is left on the tire. SDV equipment sensors 315 may include electronic sensors that detect how much padding is left of brake calipers on disk brakes. SDV equipment sensors 315 may include drivetrain sensors that detect operating conditions within an engine (e.g., power, speed, revolutions per minute—RPMs of the engine, timing, cylinder compression, coolant levels, engine temperature, oil pressure, etc.), the transmission (e.g., transmission fluid level, conditions of the clutch, gears, etc.), etc. SDV equipment sensors 315 may include sensors that detect the condition of other components of the SDV 202, including lights (e.g., using circuitry that detects if a bulb is broken), wipers (e.g., using circuitry that detects a faulty wiper blade, wiper motor, etc.), etc. Thus, in one or more embodiments of the present invention, if the SDV 202 is suffering from a certain deficiency such as having tires with little tread remaining, then the supervisory computer 201 may prevent the SDV 202 from picking up a fragile passenger (e.g., a passenger that has a neck injury, a profile of anxiety, etc. that would be exacerbated if the SDV 202 suffers a blowout). This passenger information can be retrieved from a profile database about a particular passenger (e.g., passenger 204) by the supervisory computer 201. Similarly, if the SDV equipment sensors detect that the engine is overheating and the SDV 202 is likely to be delayed when traveling from a pickup location (not shown) to destination location 206, then the supervisory computer 201 may prevent the SDV 202 from picking up a delicate passenger. Based on these factors (i.e., road conditions, SDV 202 conditions, fragility of the passenger 204), logic such as adjusted passenger monitoring system 214 within the SDV 202 and/or supervisory computer 201 may decide whether or not to pick up the passenger 204, based on whether doing so would place the passenger 204 at an undue risk of injury or emotional trauma while riding in SDV 202.

In one or more embodiments of the present invention, also within SDV 202 is a communications transceiver 317, which is able to receive and transmit electronic communication signals (e.g., RF messages) from and to other communications transceivers found in other vehicles, servers, supervisory computers, etc.

In one or more embodiments of the present invention, also within SDV 202 is a telecommunication device 325 (e.g., a smart phone, a cell phone, a laptop computer, etc.), which may be connected (e.g., via Bluetooth™ connection) to the SDV on-board computer 301.

In one or more embodiments of the present invention, also within SDV 202 is a motion detector 327, which detects movement of the passenger 204 and/or primary passenger 208 (e.g., using an optical, microwave, or acoustic sensor that detects movement based on changes in the optical, microwave, or acoustic field) within the cabin of SDV 202.

In one or more embodiments of the present invention, also within SDV 202 is a speaker 337, which is able to generate an alert to passenger 204 and/or primary passenger 208, that lets passenger 204 and/or primary passenger 208 know that SDV 202 is changing a route to drop off passenger 204 first, has arrived at destination location 206, etc.

In one or more embodiments of the present invention, the SDV utilizes a subsystem (local or on the cloud) that learns what kinds of passengers (cohorts) are more forgetful regarding passenger 204 located in the back of SDV 202 (e.g. people that are rushed, people who are used to a certain travel routine, etc.) and then adjusts its sensitivity and risk assessment accordingly. Thus, this additional individual or cohort information can be used to boost an SDV vigilance level V, with respect to how sensitive the SDV is when detecting and addressing the presence of passenger 204. The vigilance level V may vary between locations, times of year (e.g. seasons), holidays, days of the week, time of day (including brightness of day and darkness of night), weather, cognitive state of primary passenger 208, trip destinations (train station, airport), etc. Cognitive states may be estimated, with confidence level C, based on facial expressions, distraction levels (e.g., looking outside or staring at a device, talking with others, listening to music, continually talking, etc.).

In other embodiments/examples, one or more processors boost (i.e., increase) the SDV vigilance level V based on a current time of year (e.g., a holiday season), a current level of darkness around the SDV (e.g., nighttime, unlit streets, broad daylight, etc.), current weather conditions around the SDV (e.g., rainy, snowy, etc.), a current time of day, and a cognitive state of the passenger 204 and/or the primary passenger 208.

In one or more embodiments of the present invention, the estimation of the SDV primary passenger's cognitive state is based on a distraction level of the SDV primary passenger 208. That is, various current distraction levels (e.g., caused by the SDV passenger looking outside of the SDV or staring at a handheld device such as a phone, talking with others, listening to music, continually talking, a commotion outside the SDV, etc.) are identified (e.g., by the passenger sensor(s) 219), quantified (i.e., assigned a value), and weighted (using predefined weighting values). These identified and weighted quantified values provide a value that, when compared to a predetermined value (e.g., as established by historical trials), leads to a distraction level of the SDV primary passenger 208. Based on this determined distraction level, the vigilance level V of the system (e.g., monitoring and alert generation using logic within supervisory computer 201) is adjusted for the adjusted passenger monitoring system 214, in order to ensure that passenger 204 is taken to the correct location/destination. That is, when the vigilance value V is large, is might be likely that the SDV 202 could drop off the primary passenger 208 and not take into account that the other passenger 204 might be left in the SDV 202.

The personal assessment (i.e., detection and identification of passenger 204) may involve any of: reading a person's ID from an electronic identifier, such as an RFID chip in the possession of passenger 204, movement characteristics of passenger 204, facial recognition of passenger 204 (as detected by passenger sensor(s) 219 when configured as a camera), ID badge recognition, smartphone recognition, weight of passenger as detected by a scale in the seat, etc.

Figure 4:
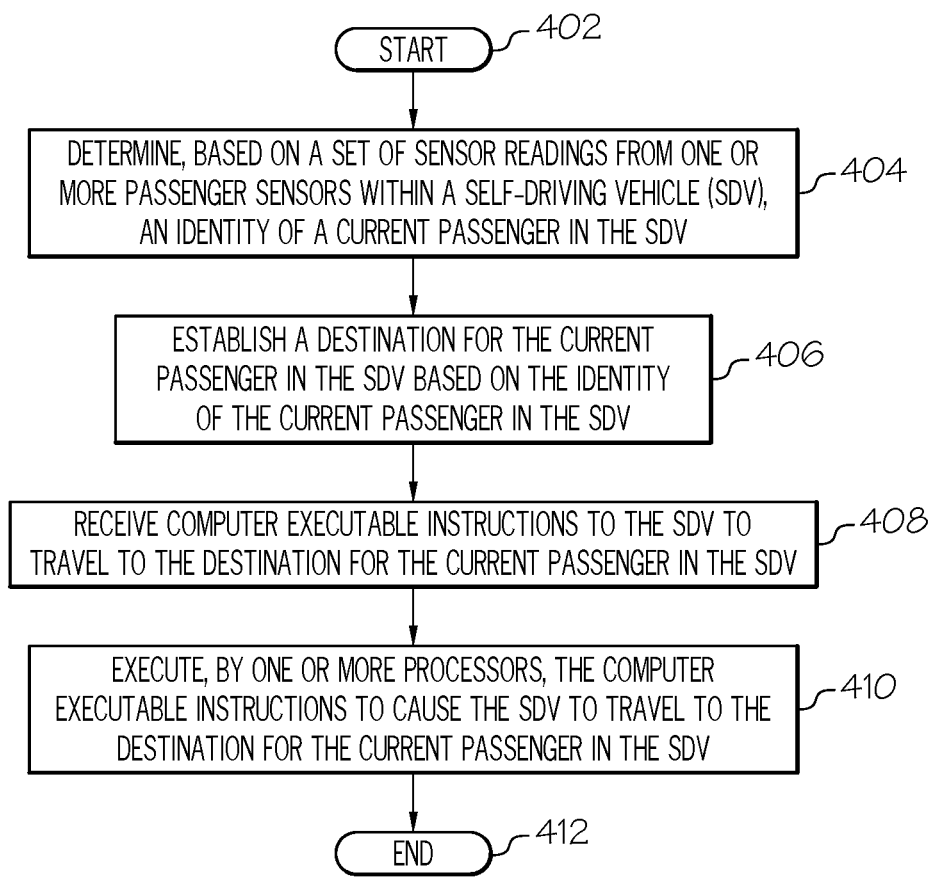
FIG. 4 is a high-level flow chart illustrating a process in accordance with one or more embodiments of the present invention.

With reference now to FIG. 4, a high-level flow chart of one or more steps performed by one or more processors and other hardware devices to control operation of a self-driving vehicle is presented in accordance with one or more embodiments of the present invention.

After initiator block 402, one or more processors (e.g., within supervisory computer 201 and/or SDV on-board computer 301) determine, based on a first set of sensor readings from one or more passenger sensors (e.g., passenger sensor(s) 219 shown in FIG. 2) within a self-driving vehicle (e.g., SDV 202), an identity of a current passenger (e.g., passenger 204) in the SDV, as described in block 404. That is, the passenger sensor(s) use visual image recognition, voice recognition, scent recognition, weight, etc. to match sensor readings to a database. By matching these sensor readings to a particular person, the system is able to 1) identity the passenger, 2) identify a (emotional and/or physiological) profile of the passenger, and/or 3) retrieve information (e.g., from a digital calendar) regarding where the passenger 204 should be taken by the SDV 202.

Thus, and as described in block 406, the processor(s) establish a destination for the current passenger in the SDV based on the identity of the current passenger in the SDV. For example, passenger 204 may have a routine of always being taken to a particular location on a certain time/day of the week. If SDV 202 picks up passenger 204 at that time/day of the week, then SDV on-board computer 301 will automatically generate instructions to the SDV control processor 303 to drive the SDV 202 to that particular location, before taking the primary passenger 208 to his/her original destination location.

As described in block 408, one or more processors (e.g., within SDV control processor 303) receive these computer executable instructions directing the SDV to travel to the destination for the current passenger in the SDV, which are then executed by SDV control processor 303, causing the SDV 202 to travel to the destination for the current passenger in the SDV (block 410).

The flow chart ends at terminator block 412.

In an embodiment of the present invention, the processor(s) (e.g., in supervisory computer 201 and/or SDV on-board computer 301) determine, based on a second set of sensor readings from the one or more passenger sensors within the self-driving vehicle SDV, a current emotional state of the current passenger in the SDV. For example, assume that passenger sensor(s) 219 visually or aurally detect that passenger 204 is a sleeping child. In response to making this detection, the processor(s) will modify the destination for the current passenger in the SDV based on the current emotional state of the current passenger in the SDV, in order to create a new destination (e.g., a nursery, home, etc.) for the current passenger in the SDV. The processor(s) thus generate computer executable instructions to the SDV to travel to the new destination for the current passenger in the SDV. The processor(s) then execute the computer executable instructions to cause the SDV to travel to the new destination for the current passenger in the SDV. In a preferred embodiment, a third party (e.g., a parent, friend, sibling, health care workers at an emergency room, etc. of the passenger 204) is notified of the new location to which the passenger 204 is being transported.

In an embodiment of the present invention, one or more processors determine, based on a third set of sensor readings from the one or more passenger sensors within the SDV, a current physiological state of the current passenger in the SDV. The processor(s) then modify the destination for the current passenger in the SDV based on the current physiological state of the current passenger in the SDV in order to create a new destination for the current passenger in the SDV. The processor(s) generate a third set of computer executable instructions to the SDV to travel to the new destination for the current passenger in the SDV, and then execute the third set of computer executable instructions to cause the SDV to travel to the new destination for the current passenger in the SDV. For example, assume that passenger sensor(s) 219 capture an image of passenger 204 bleeding. Alternatively, passenger sensor(s) 219 may receive signals from a biometric sensor being worn by passenger 204 indicating that passenger 204 is in cardiac distress. As such, the original destination location will be changed to a new destination location (e.g., a hospital). In an embodiment of the present invention, all passengers (e.g., both passenger 204 and primary passenger 208) are notified about the new destination of the SDV 202.

In an embodiment of the present invention, the destination for the current passenger is a first destination. One or more processors receive a second set of computer executable instructions to travel to a second destination. However, the processor(s) override the second set of computer executable instructions with the first set of computer executable instructions based on the identity of the current passenger in the SDV. For example, assume that a person (e.g., passenger 204, primary passenger 208, an operator of supervisory computer 201, etc.) has sent a signal to the SDV on-board computer 301 to take passenger 204 to a different location than where the passenger 204 should actually be going (e.g., according to the wishes of a parent, caretaker, etc.). For example, assume that passenger 204 is a child who would rather go to the park than to school. If passenger 204 tries to override the instructions to go school with new instructions to the SDV on-board computer 301, these new instructions are overridden, and the SDV 202 will travel to the originally-programmed destination location 206, based on his/her identity.

In an embodiment of the present invention, the destination for the current passenger is a first destination. One or more processors retrieve a location of an appointment for the current passenger in the SDV from a calendar entry in an electronic calendar for the current passenger in the SDV. The processor(s) generate a second set of computer executable instructions to travel to the location of the appointment for the current passenger in the SDV that is retrieved from the electronic calendar. The SDV on-board computer 301 then overrides the first set of computer executable instructions and executes the second set of computer executable instructions based on the calendar entry in the electronic calendar for the current passenger in the SDV. That is, the passenger 204 may have wanted to go to one location (e.g., the movies). However, passenger 204 may have forgotten that he/she has an important meeting at the office (as shown in his/her electronic calendar). As such, the SDV will take the passenger 204 to his/her office.

In an embodiment of the present invention, the electronic calendar for the passenger (passenger 204 and/or primary passenger 208) in the SDV 202 contains overlapping appointments. In this embodiment, assume that a priority level has been set and entered for each of the overlapping appointments. For example, assume that a first appointment set at a certain time has a priority level of "high", while a second appointment set at that same certain time has a priority level of "low". As such, the SDV on-board computer 301 will read (e.g., from metatags associated with the appointment entries) that the SDV 202 should be driven to the location of the first appointment, rather than to the location of the second appointment.

In an embodiment of the present invention, one or more processors identify a passenger type of the current passenger in the SDV. The processor(s) adjust a passenger monitoring system in the SDV based on the passenger type, where adjusting the passenger monitoring system modifies an SDV vigilance level V of the passenger monitoring system in the SDV to create an adjusted passenger monitoring system (e.g., adjusted passenger monitoring system 214 shown in FIG. 2). The processor(s) receive an evaluation of the current passenger from the adjusted passenger monitoring system, and determine a problem with the current passenger based on the evaluation of the current passenger from the adjusted passenger monitoring system. The processor(s) then adjust an operation of the SDV based on the determined problem with the current passenger of the SDV. For example, assume that an initial version of adjusted passenger monitoring system 214 determines that passenger 204 is a small child. In response to making this determination, the initial version of adjusted passenger monitoring system 214 is upgraded to create the adjusted passenger monitoring system 214, which has variable thresholds for actions. Thus, while the initial version of the monitoring system would not do anything if the passenger sensor(s) 219 detected arms flailing (e.g., by the child dancing in the seat to music), if the passenger 204 is someone with a history of a neurological disorder, then the passenger sensor(s) and adjusted passenger monitoring system 214 will be more responsive to such movements, and will adjust the operation of the SDV accordingly (e.g., re-routing the SDV to a hospital) because the small child might be incapacitated and not be able to reprogram the SDV to drive to a location other than the previously set destination location 206.

In an embodiment of the present invention, the processor(s) boost the SDV vigilance level V based on one or more factors from a group consisting of a current time of year, a current level of darkness around the SDV, current weather conditions around the SDV, a current time of day, calendar entries, and a cognitive state of the current passenger. For example, if it is nighttime, or raining, or early in the morning, or the passenger 204 is asleep, then the adjusted passenger monitoring system 214 will react more quickly to any anomalous movement (e.g., thrashing) by passenger 204.

In an embodiment of the present invention, the passenger type is determined based on one or more passenger features from a group consisting of a passenger's identity and a passenger's visible characteristics. That is, the "passenger type" can be retrieved from a lookup table based on the passenger's identity, or the "passenger type" can be determined based on the physical appearance of the passenger (e.g., bleeding, age, etc.).

Thus, in an embodiment of the present invention, the determined problem with the current passenger is the current passenger being asleep, and thus cannot exit the SDV 202 when the SDV 202 reaches the passenger's destination.

In another embodiment of the present invention, the determined problem with the current passenger is the current passenger having a life-threatening medical episode.

In an embodiment of the present invention, the processor(s) transmit a description of a current emotional state of the current passenger in the SDV to a third party. For example, assume that adjusted passenger monitoring system 214 detects (using sensor readings form passenger sensor(s) 219) that passenger 204 is asleep. A message is sent (e.g., to a smart phone carried by a third party) that passenger 204 is asleep.

In an embodiment of the present invention, one or more processors determine, based on sensor readings from the one or more passenger sensors, a current physiological state of the current passenger in the SDV, and then transmit a description of the current physiological state of the current passenger in the SDV to a third party. For example, if the passenger sensor(s) 219 detect that passenger 204 is having trouble breathing (based on digital video images captured by passenger sensor(s) 219), then a message may be sent to a third party's smart phone describing this real time problem.

In an embodiment of the present invention, one or more passenger sensors (e.g., passenger sensor(s) 219) generate a digital image of the current passenger in the SDV, and then transmit the digital image of the current passenger in the SDV to a third party. That is, rather than just sending a text message that states "Passenger 204 is having trouble breathing," a video of passenger 204 is sent to the third party in real time as passenger 204 is having trouble breathing, thus aiding health care workers at the destination of the SDV 202 during triage operations.

In an embodiment of the present invention, passenger sensor(s) 219 generate a chemical signature of air within the SDV. One or more processors (e.g., using communications transceiver 317 shown in FIG. 3) then transmit the chemical signature of the air within the SDV to a third party. For example, assume that passenger sensor(s) 219 include a chemical sensor that uses known chemical detection technology to identify the smell of exhaust fumes within the cabin of SDV 202. Once detected, this chemical signature (a digital representation of components found in the exhaust fumes) is sent to a third party, in order to allow the third party to take ameliorative steps, such as notifying first responders, etc. In an embodiment of the present invention, the ameliorative step includes opening the windows (e.g., by SDV on-board computer 301) on the SDV 202.

In an embodiment of the present invention, in response to determining the identity of the current passenger in the SDV, one or more processors (e.g., within SDV on-board computer 301) stop the SDV for a predetermined length of time. For example, if the SDV on-board computer 301 determines, based on video images from passenger sensor(s) 219, that passenger 204 is not authorized to ride in SDV 202, then the SDV on-board computer 301 will direct the SDV control processor 303 to pull the SDV 202 over and stop in a safe location.

In an embodiment of the present invention, one or more processors determine that the destination for the current passenger has been passed without the current passenger egressing the SDV. In response to determining that the current passenger did not egress the SDV at the destination, the processor(s) flash a light inside the SDV. That is, the SDV will generate a visual signal to the passenger 204 by causing a warning light (e.g., warning light 210 shown in FIG. 2) to start flashing, thus letting passenger 204 know that he missed his stop.

In an embodiment of the present invention, one or more processors determine that the current passenger has not exited the SDV while the SDV is at the destination of the passenger. In response to determining that the current passenger has not exited the SDV at the destination, the processor(s) flash a light, sound an aural message, etc., thus prompting the passenger to exit the SDV 202 at his/her intended destination.

In an embodiment of the present invention, one or more processors determine that the destination for the current passenger has been passed without the current passenger egressing the SDV. In response to determining that the current passenger did not egress the SDV at the destination, the processor(s) generate and execute computer readable instructions to the SDV to return to the destination. That is, if passenger 204 did not get out of the SDV 204 at the destination location 206, and logic within the SDV 204 (e.g., adjusted passenger monitoring system 214 using readings form the passenger sensor(s) 219) determines that passenger 204 is still inside SDV 204), then the adjusted passenger monitoring system 204 directs the SDV on-board computer 301 to drive the SDV 202 back to the destination location 206.

In an embodiment of the present invention, the current passenger (e.g., passenger 204) is a first passenger in the SDV 202, a primary passenger (e.g., primary passenger 208) in the SDV 202 is a second passenger in the SDV 202, and the destination for the first passenger is a first destination (e.g., daycare if the passenger 204 is a child). In this embodiment, one or more processors receive a second set of computer executable instructions to travel to a second destination for the second passenger in the SDV. For example, the primary passenger 208 may direct the system to drive the SDV 202 to his/her office. However, the one or more processors override the second set of computer executable instructions with the first set of computer executable instructions based on the identity of the first passenger in the SDV, such that the first passenger is taken to the first destination before the second passenger is taken to the second destination. That is, even though the primary passenger 208 directed the SDV on-board computer 301 to drive the SDV 202 to his/her office, the passenger sensor(s) 219 will recognize the presence of the first passenger (passenger 204), and thus will direct the SDV 202 to drive to the appropriate destination (e.g., daycare) for the first passenger.

The present invention may be implemented in one or more embodiments using cloud computing. Nonetheless, it is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
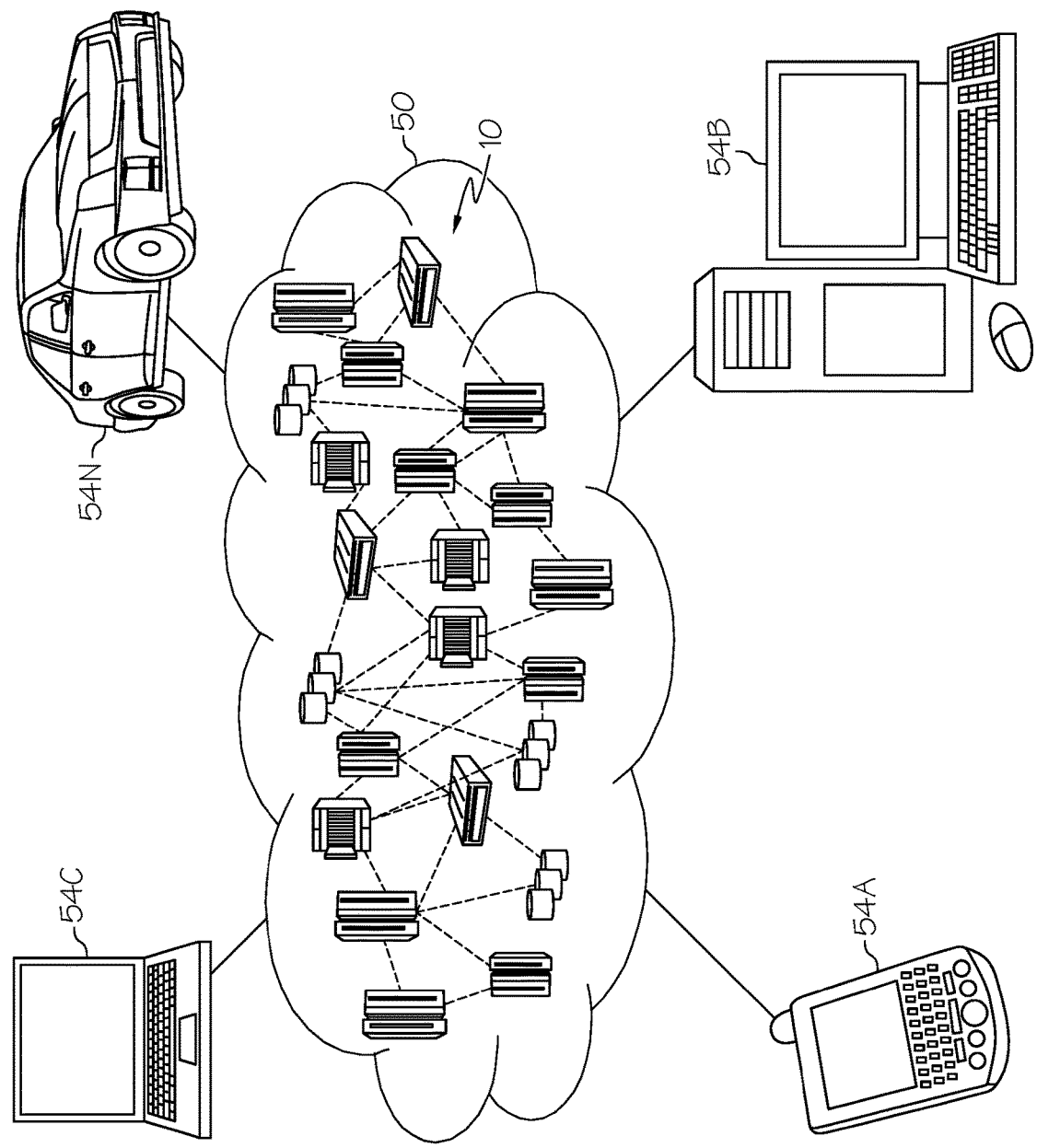
FIG. 5 depicts a cloud computing environment according to an embodiment of the present invention.

Referring now to FIG. 5, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 5 are intended to be illustrative only and that computing nodes 10 and cloud computing environment 50 can communicate with any type of computerized device over any type of network and/or network addressable connection (e.g., using a web browser).

Figure 6:
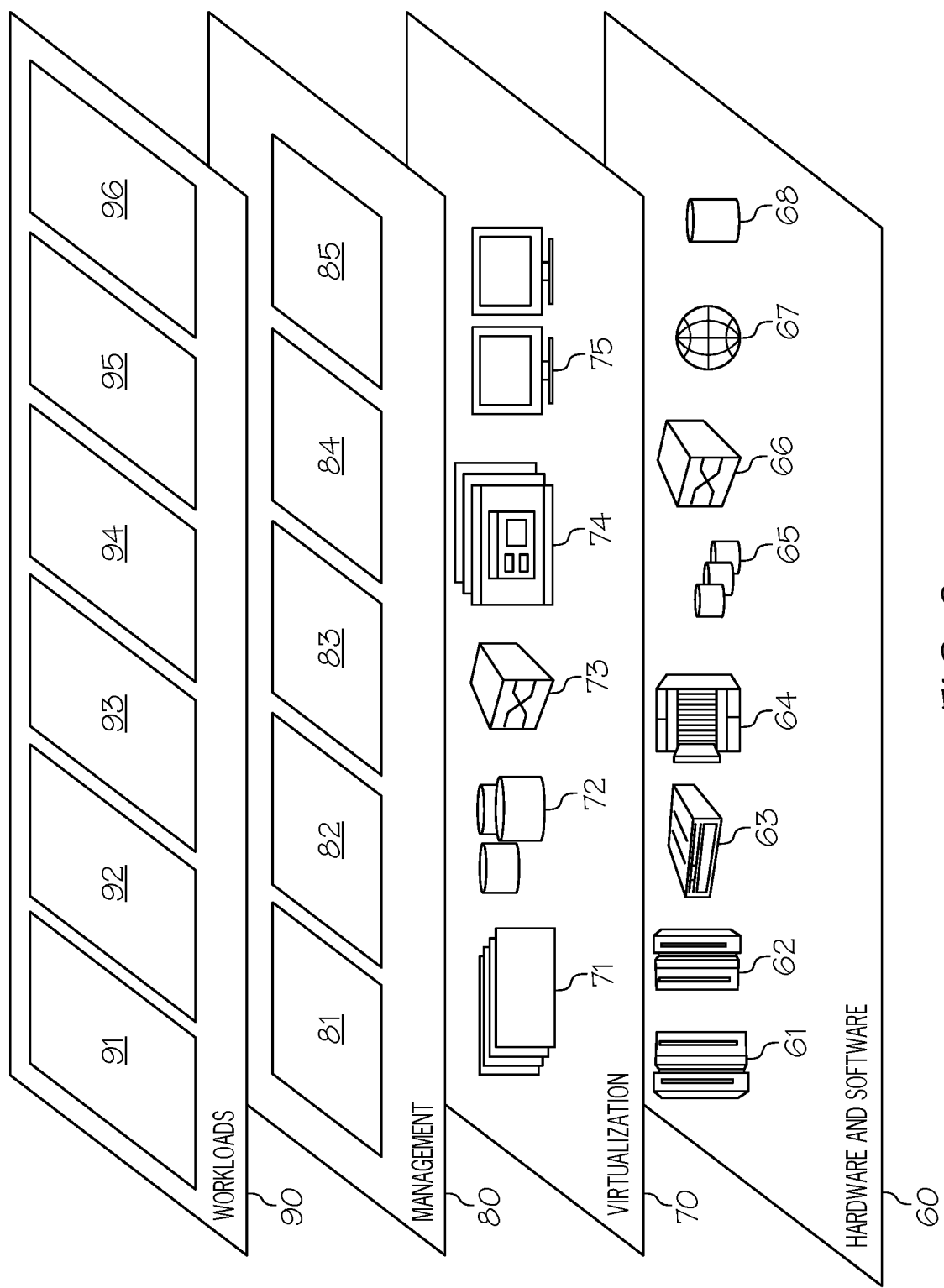
FIG. 6 depicts abstraction model layers of a cloud computing environment according to an embodiment of the present invention.

Referring now to FIG. 6, an exemplary set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and SDV control processing 96, in accordance with one or more embodiments of the present invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

The present invention may be implemented through the use of a Very High Speed Integrated Circuit (VHSIC) Hardware Description Language (VHDL) program. VHDL is an exemplary design-entry language for describing an integrated circuit, such as a Field Programmable Gate Arrays (FPGA), Application Specific Integrated Circuit (ASIC), and other similar electronic devices. In other words, and by way of example only, a software-implemented method according to one or more embodiments of the present invention may be emulated by a hardware-based VHDL program, which is then implemented in an VHSIC, such as a FPGA.

Having thus described embodiments of the present invention, in detail and by reference to illustrative embodiments thereof, it will be apparent that modifications and variations are possible without departing from the scope of the present invention defined in the appended claims.

What is claimed is:

1. A computer-implemented method of controlling a self-driving vehicle, the computer-implemented method comprising:
    determining, by one or more processors and based on a set of facial recognition sensor readings from a camera within a self-driving vehicle (SDV), an identity of a current passenger in the SDV;
    determining, by one or more processors and based on a set of biometric sensor readings from a biometric sensor for the current passenger in the SDV, a current physiological state of the current passenger in the SDV;
    determining, by one or more processors and based on a set of sleeping state readings from a video camera within the self-driving vehicle, a current sleeping state of the current passenger in the SDV;
    establishing, by one or more processors, a destination for the current passenger in the SDV based on the identity of the current passenger in the SDV, the current physiological state of the current passenger in the SDV, and the current sleeping state of the current passenger in the SDV;
    receiving, by one or more processors, a first set of computer executable instructions directing the SDV to travel to the destination for the current passenger in the SDV; and
    executing, by one or more processors, the first set of computer executable instructions to cause the SDV to travel to the destination for the current passenger in the SDV.

2. The computer-implemented method of claim 1, wherein the destination for the current passenger is a first destination, and wherein the computer-implemented method further comprises:
    receiving, by one or more processors, a second set of computer executable instructions to travel to a second destination; and
    overriding, by one or more processors, the second set of computer executable instructions with the first set of computer executable instructions based on the identity of the current passenger in the SDV.

3. The computer-implemented method of claim 1, wherein the destination for the current passenger is a first destination, and wherein the computer-implemented method further comprises:
    retrieving, by one or more processors, a location of an appointment for the current passenger in the SDV from a calendar entry in an electronic calendar for the current passenger in the SDV;
    generating, by one or more processors, a second set of computer executable instructions to travel to the location of the appointment for the current passenger in the SDV that is retrieved from the electronic calendar; and
    overriding, by one or more processors, the first set of computer executable instructions and executing, by one or more processors, the second set of computer executable instructions based on the calendar entry in the electronic calendar for the current passenger in the SDV.

4. The computer-implemented method of claim 1, further comprising:
    identifying, by one or more processors, a passenger type of the current passenger in the SDV;
    adjusting, by one or more processors, a passenger monitoring system in the SDV based on the passenger type, wherein adjusting the passenger monitoring system modifies an SDV vigilance level V of the passenger monitoring system in the SDV to create an adjusted passenger monitoring system;

receiving, by one or more processors, an evaluation of the current passenger from the adjusted passenger monitoring system;

determining, by one or more processors, a problem with the current passenger based on the evaluation of the current passenger from the adjusted passenger monitoring system; and adjusting, by one or more processors, an operation of the SDV based on the determined problem with the current passenger of the SDV.

5. The computer-implemented method of claim 4, further comprising:

boosting, by one or more processors, the SDV vigilance level V based on one or more factors from a group consisting of a current time of year, a current level of darkness around the SDV, current weather conditions around the SDV, a current time of day, and a cognitive state of the current passenger.

6. The computer-implemented method of claim 4, wherein the passenger type is determined based on one or more passenger features from a group consisting of a passenger's identity and a passenger's visible characteristics.

7. The computer-implemented method of claim 4, wherein the determined problem with the current passenger is the current passenger being asleep.

8. The computer-implemented method of claim 4, wherein the determined problem with the current passenger is the current passenger having a life-threatening medical episode.

9. The computer-implemented method of claim 1, further comprising:

transmitting, by one or more processors, a description of a current emotional state of the current passenger in the SDV to a third party.

10. The computer-implemented method of claim 1, further comprising:

determining, by one or more processors and based on sensor readings from the one or more passenger sensors, a current physiological state of the current passenger in the SDV; and transmitting, by one or more processors, a description of the current physiological state of the current passenger in the SDV to a third party.

11. The computer-implemented method of claim 1, further comprising:

generating, by the one or more passenger sensors, a digital image of the current passenger in the SDV; and transmitting, by one or more processors, the digital image of the current passenger in the SDV to a third party.

12. The computer-implemented method of claim 1, further comprising:

generating, by the one or more passenger sensors, a chemical signature of air within the SDV; and transmitting, by one or more processors, the chemical signature of the air within the SDV to a third party.

13. The computer-implemented method of claim 1, further comprising:

in response to determining the identity of the current passenger in the SDV, stopping, by one or more processors, the SDV for a predetermined length of time.

14. The computer-implemented method of claim 1, further comprising:

determining, by one or more processors, that the destination for the current passenger has been passed without the current passenger egressing the SDV; and in response to determining that the current passenger did not egress the SDV at the destination, flashing, by one or more processors, a light inside the SDV.

15. The computer-implemented method of claim 1, further comprising:

determining, by one or more processors, that the destination for the current passenger has been reached without the current passenger egressing the SDV; and in response to determining that the current passenger has not egressed the SDV at the destination, generating and executing, by one or more processors, computer readable instructions for the SDV to generate an alert directing the passenger to egress the SDV at the destination.

16. The computer-implemented method of claim 1, wherein the current passenger is a first passenger in the SDV, wherein a primary passenger in the SDV is a second passenger in the SDV, wherein the destination for the first passenger is a first destination, and wherein the computer-implemented method further comprises:

receiving, by one or more processors, a second set of computer executable instructions to travel to a second destination for the second passenger in the SDV; and overriding, by one or more processors, the second set of computer executable instructions with the first set of computer executable instructions based on the identity of the first passenger in the SDV, wherein the first passenger is taken to the first destination before the second passenger is taken to the second destination.

17. A computer program product for controlling a self-driving vehicle, the computer program product comprising a computer readable storage device having program instructions embodied therewith, the program instructions readable and executable by a computer to perform a method comprising:

determining, based on a set of facial recognition sensor readings from a camera within a self-driving vehicle (SDV), an identity of a current passenger in the SDV;

determining, based on a set of biometric sensor readings from a biometric sensor for the current passenger in the SDV, a current physiological state of the current passenger in the SDV;

determining, based on a set of sleeping state readings from a video camera within the self-driving vehicle, a current sleeping state of the current passenger in the SDV;

establishing a destination for the current passenger in the SDV based on the identity, current sleeping state, and current physiological state of the current passenger in the SDV;

receiving computer executable instructions directing the SDV to travel to the destination for the current passenger in the SDV; and executing the computer executable instructions to cause the SDV to travel to the destination for the current passenger in the SDV.

18. A system comprising:

one or more processors;

one or more computer readable memories operably coupled to the one or more processors; and one or more computer readable storage mediums having program instructions stored on at least one of the one or more storage mediums for execution by at least one of the one or more processors via at least one of the one or more memories, the stored program instructions comprising:

program instructions to determine, based on a set of facial recognition sensor readings from a camera within a self-driving vehicle (SDV), an identity of a current passenger in the SDV;

program instructions to determine, based on a set of biometric sensor readings from a biometric sensor for the current passenger in the SDV, a current physiological state of the current passenger in the SDV;

program instructions to determine, based on a set of sleeping state readings from a video camera within the self-driving vehicle, a current sleeping state of the current passenger in the SDV;

program instructions to establish a destination for the current passenger in the SDV based on the identity, current sleeping state, and current physiological state of the current passenger in the SDV;

program instructions to receive computer executable instructions directing the SDV to travel to the destination for the current passenger in the SDV; and program instructions to execute the computer executable instructions to cause the SDV to travel to the destination for the current passenger in the SDV.

* * * * *